United States Patent [19]

Schott

[11] 4,192,671

[45] Mar. 11, 1980

[54] PLANT GROWTH REGULATORS

[75] Inventor: Eberhard P. Schott, Neustadt, Fed. Rep. of Germany

[73] Assignee: BASF Aktiengesellschaft, Fed. Rep. of Germany

[21] Appl. No.: 940,474

[22] Filed: Sep. 8, 1978

[30] Foreign Application Priority Data

Sep. 14, 1977 [DE] Fed. Rep. of Germany ....... 2741343

[51] Int. Cl.$^2$ .............................................. A01N 9/20
[52] U.S. Cl. ........................................ 71/121; 71/118
[58] Field of Search .............................. 71/69, 70, 121

[56] References Cited

U.S. PATENT DOCUMENTS

| | | | |
|---|---|---|---|
| 2,689,789 | 9/1954 | Mowry et al. | 71/121 |
| 3,671,219 | 6/1972 | Nickell | 71/121 |
| 3,867,127 | 2/1975 | Fischer | 71/70 |
| 3,923,495 | 12/1975 | Alt et al. | 71/70 |
| 3,986,863 | 10/1976 | Fischer | 71/121 |

OTHER PUBLICATIONS

Lindner et al., "Comparative Inhibition of Virus, etc.;" (1959), CA 54, pp. 7043-7044 (1960).
Vetter et al., "Chemistry of Aminoarsines et al.," (1964), CA 61, pp. 8337-8338 (1964).
Cutler et al., "Alkyl Benzyldimethylammonium, etc.," (1967), CA 67, No. 31865y (1967).
Schott, "Versuchsergebenisse mit meuer, etc.," (1976), Med. Fac. Landbouww Rijksuniv. Gent, pp. 1073-1085 (1976).

*Primary Examiner*—Glennon H. Hollrah
*Attorney, Agent, or Firm*—Keil & Witherspoon

[57] ABSTRACT

Agents for regulating plant growth, especially for improving abscission, which contain substituted ammonium salts or substituted fatty acid amides, and a process for improving abscission with these agents.

1 Claim, No Drawings

PLANT GROWTH REGULATORS

The present invention relates to agents for regulating plant growth, especially in citruses, and specifically for reducing the adherence of the citrus fruits to the plants, which contain substituted N-benzylammonium salts or a substituted fatty acid amide.

In harvesting tree fruit, the fruit must be picked from the tree, i.e., the fruit must be removed from the stalk it hangs from, or the stalk of the fruit must be removed from the branch it hangs from. If the fruit is harvested not by hand but mechanically, e.g., by shaking the tree, then it is important for the success of this measure how strong the attachment is between fruit and tree.

If the fruit is tenacious, it can only be harvested by shaking the tree very vigorously. However, this damages the tree considerably, because numerous branches are broken off and the roots may be loosened.

If the fruit drops easily, it can be harvested by slight shaking of the tree. However, in this case the danger of preharvest drop is imminent, for instance when the branches are swayed by the wind. There is therefore a need for agents after the application of which the foliage and unripe fruit remain firmly attached to the branches, and the ripe fruit has only a weak attachment to the tree. Such agents are also termed abscission accelerators.

Med. Fac. Landbouww. Rijksuniv. Ghent, 41/2, 1073–1085, 1976, discloses that oxyalkylated alkylphenols, in aqueous solution in concentrations of from 500 to 20,000 ppm, significantly improve the abscission of olives.

It is also stated in the same publication that substituted N-benzylammonium salts do not have such an action, or only to a very slight extent.

I have now found that compounds selected from the group consisting of N,N-dimethyl-N-$C_{12}$-$C_{14}$-alkyl-N-benzylammonium salt, N,N-dimethyl-N,N-dibenzylammonium salt and fatty acid-N-$\beta$-hydroxyethyl-N-$\beta$-aminoethylamide significantly improve the abscission of fruit, especially citrus fruit.

Salts are generally salts of inorganic or organic acids, e.g., hydrochloric acid, hydrobromic acid, sulfuric acid, phosphoric acid, nitric acid, formic acid, acetic acid, propionic acid, and dodecylbenzenesulfonic acid.

Examples of $C_{12}$–$C_{14}$ alkyl radicals are n-dodecyl and n-tetradecyl.

Examples of fatty acids are linear, saturated or unsaturated carboxylic acids of 16 to 18 carbon atoms.

Examples of citrus fruits are oranges, bitter oranges, grapefruit, limes, tangerines, and lemons.

The promotion of abscission is of considerable economic importance. Continuously rising labor costs for conventional manual harvesting can be offset, as is known, by mechanization. However, a condition for this is that suitable abscission agents are used. Consequently, the new agents may improve the harvesting of commercial crops, e.g., citruses, coffee, pomes, drupes, indehiscent and aggregate fruit, especially when they are harvested mechanically.

The improvement in abscission also reduces the losses incurred in manual harvesting as a result of damage to the fruit and branches and the frequently ensuing fungus attack.

The following examples demonstrate the use and advantages of the new agents.

EXAMPLE 1

The results given in Table 1 show the following picture. Active ingredient D according to the invention reduces fruit retention from 100% (prior art compounds A, B and C) to 0%. There is no premature fruit drop. The fruit are still on the tree on the day of harvest and can readily be harvested with suitable mechanical equipment. Active ingredient D results in no inferior quality windfall.

Occasionally, slight to medium burns may appear on the skin of the fruit after treatment with active ingredient D, but no quality-decreasing spots are formed.

Table 1

Fruit treated:
*Citrus sinensis*, var. Valencia
Treated on March 22, 1976
Harvested on March 29, 1976

| Active ingredient | Concentration ppm | Fruit retention kg | Fruit retention % | Leaf abscission % | Fruit abscission green % | Fruit abscission ripe % | Blossom abscission % | Phytotoxic damage green fruit burns | Phytotoxic damage green fruit spots | Phytotoxic damage ripe fruit burns | Phytotoxic damage ripe fruit spots | Skin damage due to abscission % |
|---|---|---|---|---|---|---|---|---|---|---|---|---|
| Untreated | — | 11.273 | 100 | 0 | 0 | 0 | 0 | 1.0 | 1.0 | 1.0 | 1.0 | 10 |
| A prior art | 468 | 11.273 | 100 | 1.5 | 0 | 0 | 0 | 1.0 | 1.0 | 1.0 | 1.0 | 0 |
| B prior art | 464 | 11.273 | 100 | 0 | 0 | 0 | 0 | 1.0 | 1.0 | 1.0 | 1.0 | 0 |
| C prior art | 398 | 11.273 | 100 | 1.5 | 0 | 0 | 0 | 1.0 | 1.0 | 1.0 | 1.0 | 0 |
| D | 438 | 0 | 0 | 1.5 | 1.5 | 0 | less than 1 | 6.0 | 1.0 | 3.5 | 1.0 | 0 |

Active ingredient A = oxyalkylated isooctylphenol, obtained by reaction of 1 mole of isooctylphenol with about 50 moles of ethylene oxide
Active ingredient B = oxyalkylated isononylphenol, obtained by reaction of 1 mole of isononylphenol with about 20 moles of ethylene oxide
Active ingredient C = oxyalkylated isooctylphenol, obtained by reaction of 1 mole of isooctylphenol with about 25 moles of propylene oxide and about 40 moles of ethylene oxide
Active ingredient D = N,N-dimethyl-N-$C_{12}$-$C_{14}$-alkyl-N-benzylammonium chloride

EXAMPLE 2

The results given in Table 2 present the following picture. Not only active ingredient D, but also active ingredients E and F decrease fruit retention considerably: the force required by mechanical harvesting equipment to pluck off loosened fruit is less than the maximum force of 3.5 kg.

As in Example 1, there is no premature fruit drop, and no windfall.

The three active ingredients D, E and F are suitable for use as abscission agents because of their good action, and are far superior to the prior art compounds A, B and C. Furthermore, they are excellently tolerated by the crop plants.

The active ingredients are readily soluble in water. Application may be effected for instance in the form of directly sprayable aqueous solutions, suspensions, dispersions, emulsions, oil dispersions and dusts by spraying, atomizing, watering, etc. In any case, the forms of application should ensure as fine and uniform a distribution of the agents according to the invention as possible.

Taking into account the amounts of water necessary for uniform distribution, the application rates of the active ingredients according to the invention may vary from about 0.5 to 40.0 kg/ha.

The formulations contain from 0.1 to 95, and preferably from 0.5 to 90, % by weight of active ingredient.

The active ingredients according to the invention may also be applied in combination with oils, surfactants, fungicides, insecticides, acaricides, bactericides, trace elements, fertilizers, ripening agents, growth regulators, synergists, antifoams, repellents, attractants, frost protection aids, antitranspiration agents and dyes.

Table 2

Fruit treated:
*Citrus sinensis*, var. Valencia
Treated on February 7, 1977
Harvested on February 14, 1977

| Active ingredient | Concentration ppm | Fruit retention kg | Fruit retention % | Leaf abscission % | Fruit abscission green % | Fruit abscission ripe % | Blossom abscission % | Phytotoxic damage green fruit burns 1–9 | Phytotoxic damage green fruit spots 1–9 | Phytotoxic damage ripe fruit burns 1–9 | Phytotoxic damage ripe fruit spots 1–9 | Skin damage due to abscission % |
|---|---|---|---|---|---|---|---|---|---|---|---|---|
| Untreated | — | 10.050 | 100 | 0 | — | 0 | — | — | — | 1.0 | 1.0 | 100 |
| D | 1,000 | 2.960 | 29 | 35 | — | 0 | — | — | — | 1.0 | 1.0 | 0 |
| E | 1,000 | 2.920 | 29 | more than 25 | — | 0 | — | — | — | 1.0 | 1.0 | 0 |
| F | 1,000 | 3.210 | 32 | 0 | — | 0 | — | — | — | 1.0 | 1.0 | 10 |

Active ingredient E = N,N-dimethyl-N,N-dibenzylammonium chloride
Active ingredient F = fatty acid-N-β-hydroxyethyl-N-β-aminoethylamide

I claim:

1. A process for improving the abscission of citrus fruits which comprises applying to trees bearing such fruit an effective amount of an N,N-dimethyl-N-$C_{12}$–$C_{14}$-alkyl-N-benzylammonium salt or an N,N-dimethyl-N,N-dibenzylammonium salt.

* * * * *